US008216810B2

(12) United States Patent
Lipkin et al.

(10) Patent No.: US 8,216,810 B2
(45) Date of Patent: Jul. 10, 2012

(54) MULTIPLEX SYSTEMS, METHODS, AND KITS FOR DETECTING AND IDENTIFYING NUCLEIC ACIDS

(75) Inventors: W. Ian Lipkin, New York, NY (US); Thomas Briese, White Plains, NY (US); Gustavo Palacios, New York, NY (US); Omar Jabado, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 1259 days.

(21) Appl. No.: 10/833,791

(22) Filed: Apr. 27, 2004

(65) Prior Publication Data

US 2005/0239086 A1    Oct. 27, 2005

(51) Int. Cl.
C12P 19/34     (2006.01)
C12Q 1/68      (2006.01)
C07H 21/02     (2006.01)
C07H 21/04     (2006.01)
C07H 21/00     (2006.01)

(52) U.S. Cl. ...... 435/91.2; 435/6.1; 435/6.11; 435/6.12; 435/91.1; 435/91.51; 536/23.1; 536/24.3; 536/24.33; 536/25.3

(58) Field of Classification Search .............. 435/6, 6.1, 435/6.11, 6.12, 91.1, 91.2, 183, 91.51; 436/94, 436/501; 536/23.1, 24.3, 24.33, 25.3, 25.32
See application file for complete search history.

(56) References Cited

U.S. PATENT DOCUMENTS 6,355,431 B1    3/2002   Chee et al.

OTHER PUBLICATIONS

Smith, R. D. et al. "Capillary Zone Electrophoresis and Isotachophoresis-mass Spectrometry of Polypeptides and Proteins Based Upon an Electrospray Ionization Interface," Journal of Chromatography, 480, pp. 211-232 (1989).
Li, Gang et al. "Profile of Specific Antibodies to the SARS-Associated Coronavirus," The New England Journal of Medicine, pp. 508-509 (Jul. 31, 2003).
Durand et al., Circular dichroism studies of an oligodeoxyribonucleotide containing a hairpin loop made of a hexaehtylene glycolchain confirmation and stability. Nucl. Acids Res., 18: 6353-6359, 1990.
Grese et al., Metalion-peptide interactions in the gas phase: a tandem mass spectrometry study of alkali metal cationized peptides. J. Am. Chem. Soc., 111:2835-2842, 1989.
Huber et al., High-resolution liquid chromatography of oligonucleotides on nonporous alkylated styrene-divinylbenzene copolymers. Anal. Biochem., 12:351-358, 1993.
Huber et al., High-resolution liquid chromatography of DNA fragments on non-porous poly (styrene-divinylbenzene) particles. Nuc. Acids Res., 21:1061-1066, 1993.

(Continued)

Primary Examiner — Frank W Lu
(74) Attorney, Agent, or Firm — Wilmer Cutler Pickering Hale and Dorr LLP

(57) ABSTRACT

The present invention provides systems and methods for determining the presence or absence of one or more target nucleic acid sequences in a sample. Also provided are kits comprising these systems, and uses of these systems in such applications as determining the presence or absence of at least one target nucleic acid sequence in a sample, detecting microorganism transcripts and host transcripts, differentiating microorganism transcripts from host transcripts, screening blood products, assaying a food product for contamination, assaying a sample for environmental contamination, detecting genetically-modified organisms, biodefense, forensics, and genetic-comparability studies. The present invention further provides a complex that includes a target nucleic acid sequence, a capture nucleic acid, and a reporter nucleic acid.

39 Claims, 4 Drawing Sheets

OTHER PUBLICATIONS

WHO Multicentre Collaborative Network for Severe Acute Respiratory Syndrome (SARS) Diagnosis. A multicentre collaboration to investigate the cause of severe acute respiratory syndrome. Lancet, 361:1730-1733, 2003.

Zhang et al., Single-base mutational analysis of cancer and genetic diseases using membrane bound modified oligonucleotides. Nucl. Acids Res., 19:3929-3933, 1991.

Oefner, et al., High-Performance Liquid Chromatography for Routine Analysis of Hepatitis C Virus cDNA/PCR Products. Biotechniques, 16:898, 1993.

Kokoris et al., High-throughput SNP genotyping with the Masscode system. Mol. Diagn., 5(4): 329-340, 2000.

Maniatis et al., Molecular Cloning. A Laboratory Manual, 2nd ed (Cold Spring Harbor: Cold Spring Harbor Laboratory, 1989.

Smith et al., Capillary Zone Electrophoresis and Isotachophoresis-Mass Spectrometry of Polypeptides and Proteins Based Upon an Electrospray Ionization Interface. J. Chromatog., 480:211, 1989.

Oefner et al., "High-Resolution liquid Chromatography of Fluorescent dye-labeled nucleic acids," Analytical biochemistry vol. 223, pp. 39-46 (Nov. 15, 1994).

International Search Report and Written Opinion mailed Sep. 16, 2008 for International Patent Application No. PCT/US05/014499 filed Apr. 27, 2005.

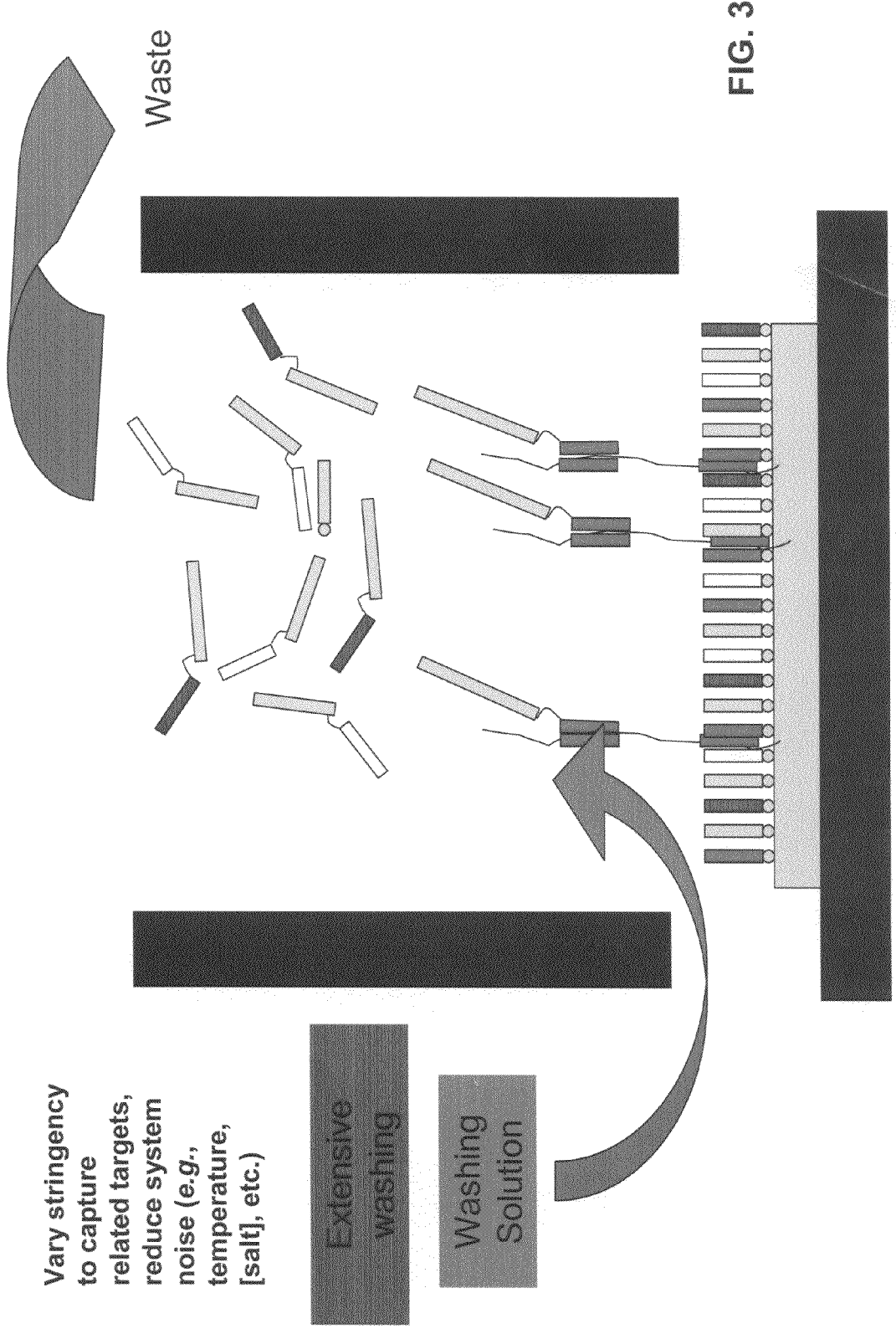

MULTIPLEX SYSTEMS, METHODS, AND KITS FOR DETECTING AND IDENTIFYING NUCLEIC ACIDS

STATEMENT OF GOVERNMENT INTEREST

This invention was made with government support under NIH Grant No. AI51292. As such, the United States government has certain rights in this invention.

BACKGROUND OF THE INVENTION

The advent of severe acute respiratory syndrome (SARS) in 2003 poignantly demonstrated the urgency of establishing rapid, sensitive, specific, and inexpensive tools for differential laboratory diagnosis of infectious diseases. Through an unprecedented global collaborative effort, the causative agent was rapidly implicated and characterized, serologic and molecular assays for infection were developed, and the outbreak was contained. Despite these successes, however, the diagnosis of SARS still rests on clinical, epidemiological, and laboratory criteria.

On Oct. 22, 2003, the World Health Organization (WHO) SARS International Reference and Verification Laboratory Network met to review the status of laboratory diagnostics in acute severe pulmonary disease. Quality assurance testing indicated that false-positive SARS coronavirus (CoV) PCR results were infrequent in network laboratories. However, participants registered concern that current assays did not allow simultaneous detection of a wide range of pathogens that could aggravate disease and/or result in clinical presentations similar to SARS. The importance of extending rapid molecular assays to include other respiratory pathogens was reinforced by the reappearance of SARS in China, and by reports of a new, highly-virulent influenza virus strain in Vietnam.

To date, there is available only a limited repertoire of sensitive, specific diagnostic assays that allow surveillance and clinical management of SARS and other pathogen-associated diseases. However, these are often not ideal. For example, immunofluorescence and enzyme-linked immunosorbent assays (ELISA) inconsistently detect antibodies to SARS-CoV before day 10 or 20 after the onset of symptoms, respectively (WHO Multicentre Collaborative Network for Severe Acute Respiratory Syndrome (SARS) Diagnosis. A multicentre collaboration to investigate the cause of severe acute respiratory syndrome. *Lancet*, 361:1730-33, 2003; Li and Xu, Profile of specific antibodies to the SARS-associated coronavirus. *N. Eng. J. Med.*, 349:5-6, 2003). Thus, although helpful in tracking the course of infection at the population level, these serologic tools have limited utility in detecting infection at early stages, when there may be potential to implement therapeutic interventions or measures (e.g., quarantine).

Contrastingly, assays based on polymerase chain reaction (PCR) have the potential to detect pathogen-associated infection at earlier time points. Indeed, methods for cloning nucleic acids of microbial pathogens directly from clinical specimens offer new opportunities to investigate microbial associations in diseases. The power of these methods lies not only in their sensitivity and speed, but also in their potential to succeed where methods for pathogen identification, through serology or cultivation, may fail because of an absence of specific reagents or because of fastidious requirements for agent replication. Various methods are currently employed for cultivation-independent characterization of infectious agents. These can be broadly segregated into methods based on direct analysis of microbial nucleic acid sequences, methods based on direct analysis of microbial protein sequences, immunological systems for microbe detection, and host-response profiling. Any comprehensive arsenal should include most, if not all, of these tools.

Multiplexing is an approach to nucleic-acid detection that uses several pooled nucleic-acid samples simultaneously, thereby greatly increasing detection speed. In current multiplex PCR systems, the use of consensus primers reduces sensitivity because: (1) binding sites are not optimized; (2) optimal primers within a consensus pool are not present at optimal concentration; and/or (3) short regions that detect all organisms within a given taxon cannot be defined. Furthermore, conventional multiplex PCR assays do not allow sensitive detection of more than 10 genetic targets. Gel-based systems are cumbersome, and are limited to visual distinction of products that differ by 20 bp. Thus, multiplexing is restricted to the number of products that can be distinguished at 20-bp intervals within the range of 100-250 bp (where amplification efficiency decreases with larger products); nesting or Southern hybridization is generally required to achieve high sensitivity.

At present, the most sensitive of all multiplex assays is real-time PCR. Real-time PCR methods have significantly changed diagnostic molecular microbiology by providing rapid, sensitive, specific tools for detecting and quantifying genetic targets. Because closed systems are employed, real-time PCR is less likely than nested PCR to be disrupted by assay contamination arising from inadvertent aerosol introduction of amplicon/positive-control/cDNA templates that can accumulate in diagnostic laboratories. Real-time PCR is also very specific. This specificity, however, is both its strength and its weakness: although the potential for false-positive signals is low, so is the utility of the method for screening to detect related, but not identical, genetic targets.

Specificity in real-time PCR is provided by two primers (each approximately 20 matching nucleotides (nt) in length), combined with a specific reporter probe of about 27 nt. The constraints of achieving hybridization at all three sites may confound detection of diverse, rapidly-evolving microbial genomes, such as those of single-stranded RNA viruses. These constraints can be compensated for, in part, by increasing numbers of primer sets accommodating various templates. However, because real-time PCR relies on fluorescent reporter dyes, the capacity for multiplexing is limited to the number of emission peaks that can be unequivocally separated. At present, up to four dyes can be identified simultaneously. Although the repertoire may increase, it is unlikely to change substantively.

In view of the foregoing, a need still exists for enhanced multiplex capacity in diagnostic molecular microbiology, including enhanced capacity to detect coinfection. As specific antiviral therapies are established, early diagnosis of infection and coinfection will become increasingly important in minimizing morbidity and mortality resulting from infectious pathogens.

SUMMARY OF THE INVENTION

The inventors have developed a novel method and fragment-length amplification reporter system (FLAReS) for multiplex amplification and size-coded identification of nucleic acid targets.

Accordingly, the present invention provides a system for determining the presence or absence of at least one target nucleic acid sequence in a sample. The system includes a plurality of subsystems, wherein each subsystem includes:

(a) a capture nucleic acid that is bound to a solid support and is capable of binding to a first region of a target nucleic acid sequence in the sample; and (b) a reporter agent that is capable of binding to a second region of the same target nucleic acid sequence in the sample. The reporter agent includes at least one reporter nucleic acid. Also provided is use of this system in at least one application selected from the group consisting of determining the presence or absence of at least one target nucleic acid sequence in a sample, detecting microorganism transcripts and host transcripts, differentiating microorganism transcripts from host transcripts, screening blood products, assaying a food product for contamination, assaying a sample for environmental contamination, detecting genetically-modified organisms, biodefense, forensics, and genetic-comparability studies.

The present invention further provides a kit for use in determining the presence or absence of at least one target nucleic acid sequence in a sample, which includes: (a) a system for determining the presence or absence of at least one target nucleic acid sequence in a sample; and (b) optionally, primers, enzyme, reagents, and/or user instructions; wherein the system includes a plurality of subsystems, and each subsystem includes: (a) a capture nucleic acid that is bound to a solid support and is capable of binding to a first region of a target nucleic acid sequence in the sample; and (b) a reporter agent that is capable of binding to a second region of the same target nucleic acid sequence in the sample, wherein the reporter agent includes at least one reporter nucleic acid.

Additionally, the present invention provides a system for determining the presence or absence of at least one target nucleic acid sequence in a sample, which includes a plurality of subsystems, wherein each subsystem includes: (a) a capture nucleic acid that is capable of binding to a first region of a target nucleic acid sequence in the sample; (b) a reporter agent that is capable of binding to a second region of the same target nucleic acid sequence in the sample, comprising at least one reporter nucleic acid; and (c) a solid support capable of specifically binding to the capture nucleic acid. Also provided is use of this system in at least one application selected from the group consisting of determining the presence or absence of at least one target nucleic acid sequence in a sample, detecting microorganism transcripts and host transcripts, differentiating microorganism transcripts from host transcripts, screening blood products, assaying a food product for contamination, assaying a sample for environmental contamination, detecting genetically-modified organisms, biodefense, forensics, and genetic-comparability studies.

The present invention further provides a kit for use in determining the presence or absence of at least one target nucleic acid sequence in a sample, which includes: (a) a system for determining the presence or absence of at least one target nucleic acid sequence in a sample; and (b) optionally, primers, enzyme, reagents, and/or user instructions; wherein the system includes a plurality of subsystems, and each subsystem includes: (a) a capture nucleic acid that is capable of binding to a first region of a target nucleic acid sequence in the sample; (b) a reporter agent that is capable of binding to a second region of the same target nucleic acid sequence in the sample, comprising at least one reporter nucleic acid; and (c) a solid support capable of specifically binding to the capture nucleic acid The present invention also provides a system for determining the presence or absence of a target nucleic acid sequence in a sample, which includes: (a) a capture nucleic acid that is bound to a solid support and is capable of binding to a first region of the target nucleic acid sequence; and (b) a reporter agent that is capable of binding to a second region of the target nucleic acid sequence, comprising at least one reporter nucleic acid. Also provided is a use of this system in at least one application selected from the group consisting of determining the presence or absence of a target nucleic acid sequence in a sample, detecting microorganism transcripts and host transcripts, differentiating microorganism transcripts from host transcripts, screening blood products, assaying a food product for contamination, assaying a sample for environmental contamination, detecting genetically-modified organisms, biodefense, forensics, and genetic-comparability studies.

Furthermore, the present invention provides a kit for use in for determining the presence or absence of a target nucleic acid sequence in a sample, which includes: (a) a system for determining the presence or absence of a target nucleic acid sequence in a sample; and (b) optionally, primers, enzyme, reagents, and/or user instructions; wherein the system includes: (a) a capture nucleic acid that is bound to a solid support and is capable of binding to a first region of the target nucleic acid sequence; and (b) a reporter agent that is capable of binding to a second region of the target nucleic acid sequence, comprising at least one reporter nucleic acid.

The present invention further provides a system for determining the presence or absence of a target nucleic acid sequence in a sample, which includes: (a) a capture nucleic acid that is capable of binding to a first region of the target nucleic acid sequence; (b) a reporter agent that is capable of binding to a second region of the target nucleic acid sequence, wherein the reporter agent includes at least one reporter nucleic acid; and (c) a solid support capable of specifically binding to the capture nucleic acid. Also provided is a use of this system in at least one application selected from the group consisting of determining the presence or absence of a target nucleic acid sequence in a sample, detecting microorganism transcripts and host transcripts, differentiating microorganism transcripts from host transcripts, screening blood products, assaying a food product for contamination, assaying a sample for environmental contamination, detecting genetically-modified organisms, biodefense, forensics, and genetic-comparability studies.

In addition, the present invention provides a kit for use in determining the presence or absence of a target nucleic acid sequence in a sample, which includes: (a) a system for determining the presence or absence of a target nucleic acid sequence in a sample; and (b) optionally, primers, enzyme, reagents, and/or user instructions; wherein the system includes: (a) a capture nucleic acid that is capable of binding to a first region of the target nucleic acid sequence; (b) a reporter agent that is capable of binding to a second region of the target nucleic acid sequence, wherein the reporter agent includes at least one reporter nucleic acid; and (c) a solid support capable of specifically binding to the capture nucleic acid.

The present invention also provides a method for determining the presence or absence of at least one target nucleic acid sequence in a sample, including the steps of: (a) obtaining a detecting system that includes a plurality of subsystems, wherein each subsystem includes: (i) a capture nucleic acid that is bound to a solid support and is capable of binding to a first region of a target nucleic acid sequence in the sample; and (ii) a reporter agent that is capable of binding to a second region of the same target nucleic acid sequence in the sample, comprising at least one reporter nucleic acid; (b) contacting the sample with the detecting system, under conditions suitable for formation of at least one complex comprising a capture nucleic acid, a reporter agent, and a target nucleic acid sequence; (c) isolating, if any, at least one complex comprising a target nucleic acid sequence, a capture nucleic acid, and a reporter nucleic acid; (d) amplifying the reporter nucleic acid or a portion thereof in the at least one complex; and (e) determining the presence or absence of the reporter nucleic acid or portion thereof; wherein the target nucleic acid sequence is present in the sample if the reporter nucleic acid or portion thereof is present, and the target nucleic acid sequence is absent from the sample if the reporter nucleic acid or portion thereof is absent.

Also provided is a method for determining the presence or absence of at least one target nucleic acid sequence in a sample, including the steps of: (a) obtaining a detecting system that includes a plurality of subsystems, wherein each subsystem includes: (i) a capture nucleic acid that is capable of binding to a first region of a target nucleic acid sequence in the sample; (ii) a reporter agent that is capable of binding to a second region of the same target nucleic acid sequence in the sample, comprising at least one reporter nucleic acid; and (iii) a solid support capable of specifically binding to the capture nucleic acid; (b) contacting the sample with the detecting system, under conditions suitable for formation of at least one complex comprising a capture nucleic acid, a reporter agent, and a target nucleic acid sequence; (c) isolating, if any, at least one complex comprising a target nucleic acid sequence, a capture nucleic acid, and a reporter nucleic acid; (d) amplifying the reporter nucleic acid or a portion thereof in the at least one complex; (e) binding the capture nucleic acid in each subsystem to the solid support of each subsystem; and (f) determining the presence or absence of the reporter nucleic acid or portion thereof; wherein the target nucleic acid sequence is present in the sample if the reporter nucleic acid or portion thereof is present, and the target nucleic acid sequence is absent from the sample if the reporter nucleic acid or portion thereof is absent.

Additionally, the present invention provides a method for determining the presence or absence of a target nucleic acid sequence in a sample, including the steps of: (a) obtaining a detecting system that includes: (i) a capture nucleic acid that is bound to a solid support and is capable of binding to a first region of the target nucleic acid sequence; and (ii) a reporter agent that is capable of binding to a second region of the target nucleic acid sequence, comprising at least one reporter nucleic acid; (b) contacting the sample with the capture nucleic acid and the reporter agent, under conditions suitable for formation of a complex comprising the capture nucleic acid, the reporter agent, and the target nucleic acid sequence; (c) isolating, if any, a complex comprising the target nucleic acid sequence, the capture nucleic acid, and the reporter nucleic acid; (d) amplifying the reporter nucleic acid or a portion thereof in the complex; and (e) determining the presence or absence of the reporter nucleic acid or portion thereof; wherein the target nucleic acid sequence is present in the sample if the reporter nucleic acid or portion thereof is present, and the target nucleic acid sequence is absent from the sample if the reporter nucleic acid or portion thereof is absent.

The present invention also provides a method for determining the presence or absence of a target nucleic acid sequence in a sample, including the steps of: (a) obtaining a detecting system comprising: (i) a capture nucleic acid that is capable of binding to a first region of the target nucleic acid sequence; (ii) a reporter agent that is capable of binding to a second region of the target nucleic acid sequence, comprising at least one reporter nucleic acid; and (iii) a solid support capable of specifically binding to the capture nucleic acid; (b) contacting the sample with the capture nucleic acid and the reporter agent, under conditions suitable for formation of a complex comprising the capture nucleic acid, the reporter agent, and the target nucleic acid sequence; (c) isolating, if any, a complex comprising the target nucleic acid sequence, the capture nucleic acid, and the reporter nucleic acid; (d) amplifying the reporter nucleic acid or a portion thereof in the complex; (e) binding the capture nucleic acid to the solid support; and (f) determining the presence or absence of the reporter nucleic acid or portion thereof; wherein the target nucleic acid sequence is present in the sample if the reporter nucleic acid or portion thereof is present, and the target nucleic acid sequence is absent from the sample if the reporter nucleic acid or portion thereof is absent.

Finally, the present invention provides a complex that includes a target nucleic acid sequence, a capture nucleic acid, and a reporter nucleic acid.

Additional aspects of the present invention will be apparent in view of the description which follows.

BRIEF DESCRIPTION OF THE FIGURES

FIG. 3 sets forth a microfluidics purification strategy for use in FLAReS.

DETAILED DESCRIPTION OF THE INVENTION

Figure 1:
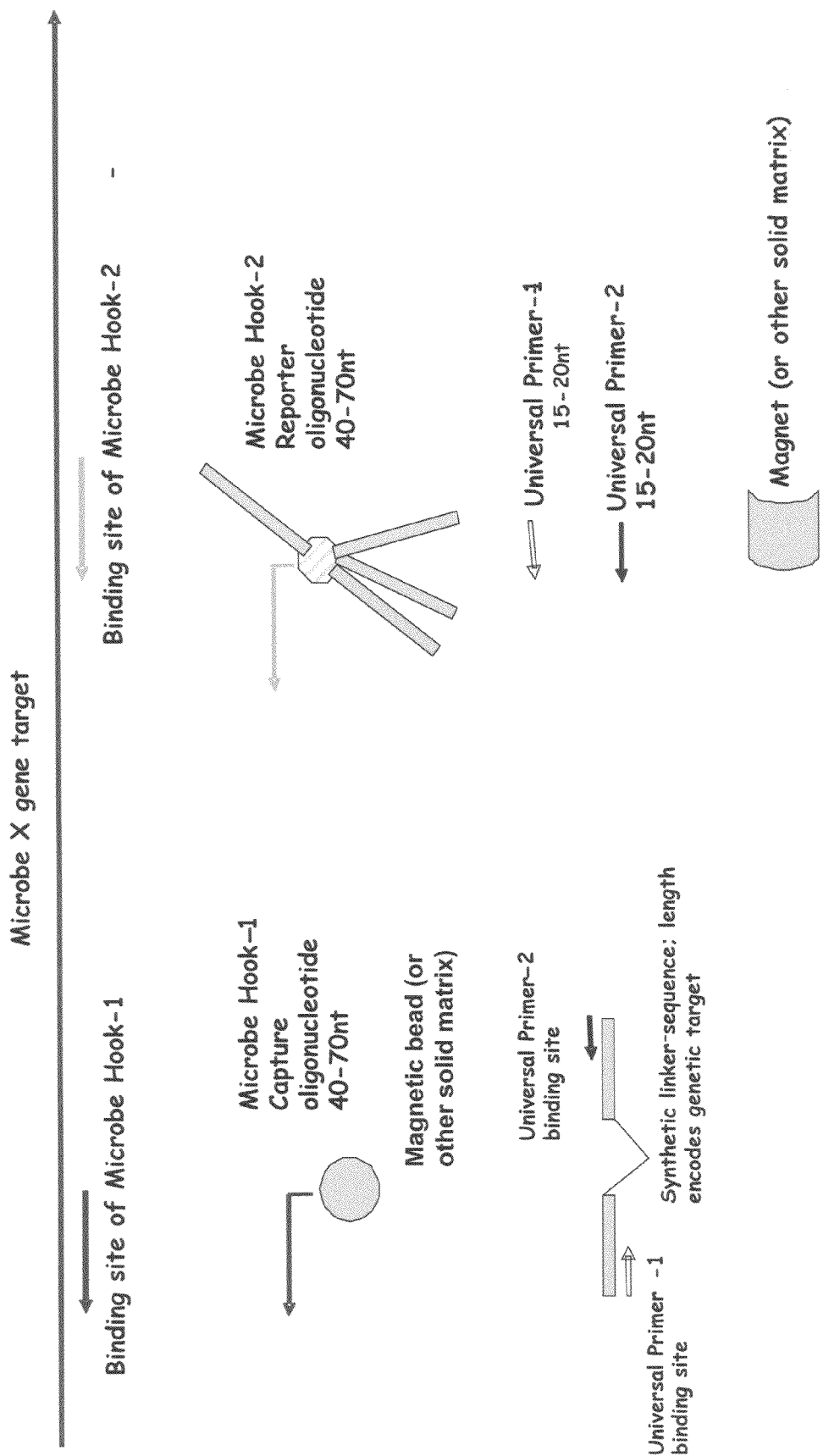
FIG. 1 illustrates components of the FLAReS system.

The inventors have developed a method and system for multiplex amplification, and size-coded identification, of nucleic acid targets. The method and system rely upon a master reagent mix and method, wherein primers, nucleotides, enzymes, and other components are present in optimal concentrations, and do not vary with the target sequence. The invention is based on a strategy for enrichment of a reporter template for use in PCR and other gene-amplification methods. This is achieved by hybridization, in solution, of two different populations of variably-degenerate polynucleotides complementary to two different regions on the same nucleic acid strand of a target sequence (e.g., a microbial genome or mRNA). One polynucleotide population (the capture polynucleotide) is immobilized on a solid support or substrate; the other population (the reporter polynucleotide) contains both a sequence complementary to a different region of the target than that of the capture polynucleotide, and a sequence that includes a polymerase binding site for initiation of PCR or isothermal amplification. Binding of both types of polynucleotides (capture and reporter) to the target sequence results in a bridge that facilitates separation of specific reporter polynucleotides from all other non-reactive reporter polynucleotides. While the sequences for amplification do not vary with the target, the template size is distinctive for each potential target. Therefore, the assay's specificity depends upon discrete changes in the length of an amplification product. This allows for size-coded identification of nucleic acid targets.

Accordingly, the present invention provides a system for determining the presence or absence of a target nucleic acid sequence (e.g., a microbe transcript, a host transcript, etc.) in a sample. In one embodiment, the target nucleic acid sequence is related to a pathological condition in a subject and/or is derived from a pathogen. Exemplary pathogens include, without limitation, pathogens implicated in encephalitis, hemorrhagic fevers, and acute, severe respiratory disease (e.g., SARS CoV and influenza viruses); *M. pneumoniae*; West Nile virus (WNV); St. Louis encephalitis virus (SLEV); Dengue type 1, 2, 3, and 4; bunyamwera and California encephalitis serogroups of the bunyaviruses; all six Venezuelan equine encephalitis virus serotypes; respiratory syncytial virus groups A and B; etc. The subject or host may be any animal, particularly a mammal, including, without limitation, a cow, dog, human, monkey, mouse, pig, or rat. Preferably, the subject is a human. The subject may be known to have a pathogen infection, suspected of having a pathogen infection, or believed not to have a pathogen infection. In one embodiment of the present invention, the biological sample is obtained from a subject suspected of having SARS.

The sample of the present invention may be an environmental sample, a food sample, a biological sample, etc. The sample may or may not comprise or contain the target nucleic acid sequence. For example, the environmental sample or the food sample may be known to have pathogen contamination, suspected of having pathogen contamination, or believed not to have pathogen contamination. The biological sample may be obtained from any tissue of a subject, and may be removed by standard biopsy. In addition, the biological sample may be a bodily fluid (e.g., blood, cerebrospinal fluid, pericardial fluid, peritoneal fluid, saliva, serum, sputum, or urine), or a solid (e.g., feces). The system of the present invention comprises: (a) a capture nucleic acid that is capable of binding to a first region of the target nucleic acid sequence; and (b) a reporter agent that is capable of binding to a second region of the target nucleic acid sequence, comprising at least one reporter nucleic acid. The first region of the target nucleic acid sequence differs from the second region of the target nucleic acid sequence. However, it is conceivable that the first and second regions of the target nucleic acid sequence could comprise the same nucleotide sequences, as genes are known to contain repeat sequences. In one preferred embodiment of the present invention, the capture nucleic acid and the reporter nucleic acid bind to the same strand (i.e., 5' or 3') of the target nucleic acid sequence.

As used herein, a "nucleic acid", or "polynucleotide", includes a nucleic acid, an oligonucleotide, a nucleotide, a polynucleotide, and any fragment, variant, or derivative thereof. The nucleic acid or polynucleotide may be double-stranded, single-stranded, or triple-stranded DNA or RNA (including cDNA), or a DNA-RNA hybrid of genetic or synthetic origin, wherein the nucleic acid contains any combination of deoxyribonucleotides and ribonucleotides and any combination of bases, including, but not limited to, adenine, thymine, cytosine, guanine, uracil, inosine, and xanthine hypoxanthine. As further used herein, the term "cDNA" refers to an isolated DNA polynucleotide or nucleic acid molecule, or any fragment, derivative, or complement thereof. It may be double-stranded, single-stranded, or triple-stranded, it may have originated recombinantly or synthetically, and it may represent coding and/or noncoding 5' and/or 3' sequences. Additionally, as used herein, the singular forms "a", "an", and "the" include plural reference, unless the context clearly dictates otherwise. For example, reference to "a nucleic acid" includes a plurality of such nucleic acids, and equivalents thereof known to those skilled in the art.

The nucleic acid or polynucleotide of the present invention may be combined with a carbohydrate, a lipid, a protein, or other materials. A nucleic acid sequence of interest may be chemically synthesized using one of a variety of techniques known to those skilled in the art, including, without limitation, automated synthesis of oligonucleotides having sequences which correspond to a partial sequence of the nucleotide sequence of interest, or a variation sequence thereof, using commercially-available oligonucleotide synthesizers, such as the Applied Biosystems Model 392 DNA/RNA synthesizer.

In one embodiment of the present invention, the capture nucleic acid is pre-bound to a solid support or substrate. Preferred solid supports include, but are not limited to, beads (e.g., magnetic beads (i.e., the bead itself is magnetic, or the bead is susceptible to capture by a magnet) beads made of metal, glass, plastic, dextran (such as the dextran bead sold under the tradename, Sephadex (Pharmacia)), silica gel, agarose gel (such as those sold under the tradename, Sepharose (Pharmacia)), or cellulose); capillaries; flat supports (e.g., filters, plates, or membranes made of glass, metal (such as steel, gold, silver, aluminum, copper, or silicon), or plastic (such as polyethylene, polypropylene, polyamide, or polyvinylidene fluoride); a chromatographic substrate; a microfluidics substrate; and pins (e.g., arrays of pins suitable for combinatorial synthesis or analysis of beads in pits of flat surfaces (such as wafers), with or without filter plates). Additional examples of suitable solid supports include, without limitation, agarose, cellulose, dextran, polyacrylamide, polystyrene, sepharose, and other insoluble organic polymers. Appropriate binding conditions (e.g., temperature, pH, and salt concentration) may be readily determined by the skilled artisan.

In another embodiment of the present invention, the capture nucleic acid becomes bound to the solid support during use of the inventors' system. In that case, the system for determining the presence or absence of a target nucleic acid sequence in a sample would comprise: (a) a capture nucleic acid that is capable of binding to a first region of the target nucleic acid sequence; (b) a reporter agent that is capable of binding to a second region of the target nucleic acid sequence, comprising at least one reporter nucleic acid; and (c) a solid support capable of specifically binding to the capture nucleic acid. It is conceivable that two or more subsystems may share a solid support, such that the same solid support will contribute to two or more subsystems; however, each subsystem will have its own capture nucleic acid and its own reporter agent.

In the case where the capture nucleic acid is pre-bound to the solid support, and in the case where the capture nucleic acid is bound to the solid support during use of the system, the capture nucleic acid may be either covalently or non-covalently bound to the solid support. Furthermore, the capture nucleic acid may be directly bound to the solid support (e.g., the nucleotides of the capture nucleic acid are in direct van der Waal and/or hydrogen bond and/or salt-bridge contact with the solid support), or indirectly bound to the solid support (e.g., the nucleotides of the capture nucleic acid are not in direct contact with the solid support themselves). Where the capture nucleic acid is indirectly bound to the solid support, the nucleotides of the capture nucleic acid are linked to an intermediate composition that, itself, is in direct contact with the solid support.

To facilitate binding of the capture nucleic acid to the solid support, the capture nucleic acid may be modified with one or more molecules suitable for direct binding to a solid support and/or indirect binding to a solid support by way of an intermediate composition or spacer molecule that is bound to the solid support (such as an antibody, a receptor, a binding protein, an enzyme, etc.). Examples of such modifications include, without limitation, a ligand (e.g., a small organic or inorganic molecule, a ligand to a receptor, a ligand to a binding protein or the binding domain thereof (such as biotin and digoxigenin)), an antigen and the binding domain thereof, and a substrate of an enzyme.

Linkers or spacer molecules suitable for spacing biological and other molecules, including nucleic acids/polynucleotides, from solid surfaces are well-known in the art, and include, without limitation, polypeptides (e.g., polyproline, polyalanine, etc.), saturated or unsaturated bifunctional hydrocarbons (e.g., 1-amino-hexanoic acid), and polymers (e.g., polyethylene glycol, etc.) For polynucleotide compounds, a preferred linker is polyethylene glycol (MW 100 to 1000). Exemplary 1,4-dimethoxytrityl-polyethylene glycol phosphoramidites that are useful for forming phosphodiester linkages with hydroxyl groups of hydroxyl-activated beads, as well as methods for their use in nucleic acid synthesis on solid supports, are described in Zhang et al., *Nucl. Acids Res.*, 19:3929-33, 1991, and Durand et al., *Nucl. Acids Res.*, 18:6353-59, 1990, the entire contents of which are incorporated herein. Other useful linkers are commercially available.

In one embodiment of the present invention, a sequence of the capture nucleic acid of the system is the complement of (i.e., is complementary to) a sequence of the first region of the target nucleic acid sequence. In another embodiment, the capture nucleic acid of the system is capable of hybridizing to the first region of the target nucleic acid sequence under high-stringency conditions. The "complement" of a nucleic acid sequence refers, herein, to a nucleic acid molecule which is completely complementary to another nucleic acid, or which will hybridize to the other nucleic acid under conditions of high stringency. High-stringency conditions are known in the art. See, e.g., Maniatis et al., *Molecular Cloning: A Laboratory Manual*, 2nd ed. (Cold Spring Harbor: Cold Spring Harbor Laboratory, 1989) and Ausubel et al., eds., *Current Protocols in Molecular Biology* (New York, N.Y.: John Wiley & Sons, Inc., 2001). Stringent conditions are sequence-dependent, and may vary depending upon the circumstances.

In accordance with the system of the present invention, the reporter nucleic acid(s) may comprise a site of relevance in a biological process, such as amplification, transcription, or translation. Examples of such sites include, without limitation, a primer binding site (e.g., for polymerase chain reaction (PCR)), a polymerase binding site (e.g., for isothermal amplification), a transcription termination site, and a restriction enzyme site. By way of example, the reporter nucleic acid(s) may comprise at least one forward primer binding site and at least one reverse primer binding site, for use in initiating PCR amplification. Similarly, the reporter nucleic acid(s) may comprise at least one 5' primer binding site (e.g., a 5' T7 binding site) and at least one 3' transcription termination site, for use in initiating isothermal amplification. The sequences for PCR or isothermal amplification do not generally vary with the target nucleic acid sequence; rather, the template size is distinctive for each potential target (e.g., microbe or host transcript). Therefore, the system's specificity depends upon discrete changes in the length of an amplification product. This allows for size-coded identification of target nucleic acid sequences.

As disclosed herein, the reporter nucleic acid in certain embodiments may not bind to the second region of the target nucleic acid sequence itself. In these cases, the reporter nucleic acid is directly or indirectly linked to a binder nucleic acid that is capable of binding to the second region of the target nucleic acid sequence. Thus, the reporter agent would comprise both a reporter nucleic acid and a binder nucleic acid.

The reporter nucleic acid may be directly linked to the binder nucleic acid using any chemical or physical means, under conditions suitable for the formation of a reporter nucleic acid/binder nucleic acid complex, provided these means do not significantly interfere with the binding of the binding nucleic acid to the target nucleic acid. Examples of such chemical or physical means include, without limitation, nucleic acid cross-linking agents (e.g., DMP 840, 8-methoxypsoralen, cis-benzodipyrone, trans-benzodipyrone, formaldehyde, and 1,3-butadiene diepoxide) and photochemical cross-linking agents (e.g., UV-laser cross-linking).

The reporter nucleic acid may also be linked to the binder nucleic acid, covalently or non-covalently, using any suitable intermediate composition. Examples of suitable intermediate compositions include, but are not limited to, a physical substance (e.g., a solid substance, such as a bead, fiber, metal, plastic, glass, silica, and cellulose) and a chemical linker (e.g., an organic compound; an organic or inorganic polymer, such as c9; at least one amino acid; or at least one nucleotide). In one embodiment, the reporter nucleic acid and the binder nucleic acid may be joined or linked by molecule-molecule interactions. For example, one of the nucleic acids may be linked to a ligand (e.g., biotin) and the other may be linked to a binding protein/receptor (e.g., avidin). Alternatively, one of the nucleic acids may be linked to an antigen, and the other may be linked to an antibody specific for the antigen.

Where the reporter nucleic acid is linked to a binder nucleic acid, so as to facilitate binding of the reporter agent to the target nucleic acid sequence, the binder nucleic acid may comprise a sequence that is complementary to a sequence of the second region of the target nucleic acid sequence. Similarly, the binder nucleic acid may be capable of hybridizing to the second region of the target nucleic acid sequence under high-stringency conditions.

In certain other embodiments of the present invention, the reporter nucleic acid itself may comprise a sequence that is complementary to a sequence of the second region of the target nucleic acid sequence, or the reporter nucleic acid is capable of hybridizing to the second region of the target nucleic acid sequence under high-stringency conditions. In these cases, a binder nucleic acid is not required in order for the reporter agent to bind to the target nucleic acid sequence. Thus, the reporter agent would comprise at least one reporter nucleic acid, but no binder nucleic acid.

The present invention also provides a kit for use in for determining the presence or absence of a target nucleic acid sequence in a sample comprising: (a) a system for determining the presence or absence of a target nucleic acid sequence in a sample; and (b) optionally, primers, enzyme, reagents (e.g., PCR reagents), and/or user instructions, and any combination thereof. The system for determining the presence or absence of a target nucleic acid comprises: (a) a capture nucleic acid that is bound to a solid support and is capable of binding to a first region of the target nucleic acid sequence; and (b) a reporter agent that is capable of binding to a second region of the target nucleic acid sequence, comprising at least one reporter nucleic acid. The kit's instructions may include, without limitation, the conditions for performing a PCR reaction, such as annealing and extension temperatures, time periods, and number of cycles. Examples of suitable PCR reagents include, without limitation, PCR reaction buffer, $Mg^{2+}$ (e.g., $MgCl_2$), dNTPs, DNA polymerases (such as reverse transcriptases and thermostable DNA polymerases (e.g., Taq-related DNA polymerases and Pfu-related DNA polymerases)), RNase, PCR reaction enhancers or inhibitors, PCR reaction monitoring agents (e.g., double-stranded DNA dye (such as SYBR® Green), TaqMan® probes, molecular beacons, and Scorpions®), and PCR-grade water.

As disclosed herein, the inventors' system for detecting a target nucleic acid sequence in a sample is particularly useful in multiplex PCR. Accordingly, the present invention further provides a system for determining the presence or absence of one or more—preferably, multiple—target nucleic acid sequences in a sample. The system comprises a plurality of subsystems, wherein each subsystem comprises: (a) a capture nucleic acid that is pre-bound to a solid support and is capable of binding to a first region of a target nucleic acid sequence in the sample; and (b) a reporter agent that is capable of binding to a second region of the same target nucleic acid sequence in the sample, comprising at least one reporter nucleic acid. This system may be particularly useful where at least two of the subsystems are designed to detect different target nucleic acids. Thus, in one embodiment of the present invention, the capture nucleic acid and the reporter agent in at least one subsystem bind to a target nucleic acid sequence that is different from the target nucleic acid sequence to which the capture nucleic acid and the reporter agent of at least one other subsystem bind. In another embodiment, at least two of the subsystems comprise reporter nucleic acids that differ in length.

The present invention is beneficial in that it allows for the sensitive, multiplex detection and characterization of genetic targets where the precise target sequence may not be known. The present invention has numerous advantages over multiplex real-time PCR and consensus PCR. For example, the present invention uses only one set of specific primers for amplification; binding sites are optimized; the system is flexible with respect to hybrid melting temperature; optimal primers are present at optimal concentration; polynucleotides can be designed to detect all genetic targets within a given taxon, including those that may be unknown—a major advantage in pathogen surveillance and discovery; the assay is easily modified for use with various nucleic acid amplification platforms; the assay is readily adapted to field conditions; and the assay can be either qualitative or quantitative. The assay is also advantageous in that one needs only to prepare a sample; it is not necessary to open reaction tubes or otherwise interfere with the process. Thus, contamination is reduced, and ease is increased.

Modifications may be introduced into the system, as desired. For example, the specificity of the system may be altered using related, but not identical, capture nucleic acids to allow detection of sequences that differ from the ideal target. This modification is useful for the identification of novel genes or microbes. Additionally, the system may be modified to enhance the signal, using the same reporter nucleic acid in conjunction with capture nucleic acids that hybridize to different regions on the same target nucleic acid sequence. This modification is useful where targets are present in low copy number. Furthermore, the system may be modified to confirm detection of a microbe or host transcript, using two independent capture nucleic acid sets that bind different regions of the same target nucleic acid sequence and yield different amplification products.

The present invention also provides a kit for use in determining the presence or absence of one or more—preferably, multiple—target nucleic acid sequences in a sample, comprising: (a) a system for determining the presence or absence of one or more target nucleic acid sequences in a sample; and (b) optionally, primers, enzyme, reagents, user instructions, and/or any combination thereof. The system for determining the presence or absence of one or more target nucleic acid sequences in a sample comprises a plurality of subsystems; each subsystem comprises: (a) a capture nucleic acid that is bound to a solid support and is capable of binding to a first region of a target nucleic acid sequence in the sample; and (b) a reporter agent that is capable of binding to a second region of the same target nucleic acid sequence in the sample, comprising at least one reporter nucleic acid.

As discussed above, the system of the present invention is flexible enough to permit the capture nucleic acid to become bound to the solid surface while the system is in use. Therefore, the capture nucleic acid need not be pre-bound to the solid surface of the system. Accordingly, the present invention further provides a system for determining the presence or absence of one or more—preferably, multiple—target nucleic acid sequences in a sample, comprising a plurality of subsystems, wherein each subsystem comprises: (a) a capture nucleic acid that is capable of binding to a first region of a target nucleic acid sequence in the sample; (b) a reporter agent that is capable of binding to a second region of the same target nucleic acid sequence in the sample, comprising at least one reporter nucleic acid; and (c) a solid support capable of specifically binding to the capture nucleic acid.

The present invention also provides a kit for use in for determining the presence or absence of one or more—preferably, multiple—target nucleic acid sequences in a sample, comprising: (a) a system for determining the presence or absence of one or more target nucleic acid sequences in a sample; and (b) optionally, primers, enzyme, reagents, user instructions, and/or any combination thereof. The system comprises a plurality of subsystems, wherein each subsystem comprises: (a) a capture nucleic acid that is capable of binding to a first region of a target nucleic acid sequence in the sample; (b) a reporter agent that is capable of binding to a second region of the same target nucleic acid sequence in the sample, comprising at least one reporter nucleic acid; and (c) a solid support capable of specifically binding to the capture nucleic acid.

The inventors' systems for determining the presence or absence of one or more target nucleic acid sequences in a sample may be used to detect host transcripts and microorganism transcripts (e.g., transcripts of infectious pathogens that are related to differential diagnosis of respiratory disease, encephalitis, or hemorrhagic fevers), or to differentiate microorganism transcripts from host transcripts, in clinical, environmental, and food samples. Additional applications include, without limitation, detection of other infectious pathogens, the screening of blood products (e.g., screening blood products for infectious agents or for donor/recipient incompatibility), biodefense, food safety, environmental contamination, forensics, and genetic-comparability studies). Accordingly, the present invention also provides uses of the detection systems described herein in a myriad of specific applications, including, without limitation, a method for determining the presence or absence of a target nucleic acid sequence in a sample, a method for detecting microorganism transcripts and host transcripts, a method for differentiating microorganism transcripts from host transcripts, a method for screening blood products, a method for assaying a food product for contamination, a method for assaying a sample for environmental contamination, and a method for detecting genetically-modified organisms. The present invention further provides use of the system in such general applications as biodefense against bio-terrorism, forensics, and genetic-comparability studies.

The present invention also provides methods of detecting target nucleic acid sequences in a sample, using the detecting systems described herein. For example, the present invention provides a method for determining the presence or absence of a target nucleic acid sequence in a sample, comprising the steps of: (a) obtaining a detecting system, comprising: (i) a capture nucleic acid that is pre-bound to a solid support and is capable of binding to a first region of the target nucleic acid sequence; and (ii) a reporter agent that is capable of binding to a second region of the target nucleic acid sequence, comprising at least one reporter nucleic acid; (b) contacting the sample with the capture nucleic acid and the reporter agent of the detecting system, under conditions suitable for formation of a complex comprising the target nucleic acid sequence, the capture nucleic acid, and the reporter nucleic acid; (c) isolating, if any, a complex comprising the target nucleic acid sequence, the capture nucleic acid, and the reporter nucleic acid; (d) amplifying the reporter nucleic acid or a portion thereof in the complex; and (e) determining the presence or absence of the reporter nucleic acid or portion thereof. In accordance with this method, the target nucleic acid sequence is present in the sample if the reporter nucleic acid or portion thereof is present and/or is detected; the target nucleic acid sequence is absent from the sample if the reporter nucleic acid or portion thereof is absent and/or is not detected.

A sample may be contacted with the capture nucleic acid of the detecting system prior to, at the same time as, or following the contacting of the reporter nucleic acid with the sample. Thereafter, a complex comprising the target nucleic acid sequence, the capture nucleic acid, and the reporter nucleic acid may be isolated using standard molecular biology techniques. For example, where the capture nucleic acid is attached to an iron/magnetic bead, the complex may be collected using a magnet or centrifugation. The pellet may then be subjected to several round of washes, to eliminate any unbound reporter nucleic acid which could otherwise interfere with the subsequent amplification process. Additionally, where the capture nucleic acid is linked to a biotin, for example, the complex may be collected to the bottom of the wells of a 96-well plate, wherein the surfaces of the wells are coated with avidin. The complex will bind to the wells, and may then be washed several times to eliminate contamination from unbound reporter nucleic acid.

Following the isolation step, the reporter nucleic acid, or a portion thereof, in the isolate is amplified. Amplification may be carried out by any means known in the art, including polymerase chain reaction (PCR) and isothermal amplification. PCR is a practical system for in vitro amplification of a DNA base sequence. For example, a PCR assay may use a heat-stable polymerase and two ~20-base primers: one complementary to the (+)-strand at one end of the sequence to be amplified, and the other complementary to the (−)-strand at the other end. Because the newly-synthesized DNA strands can subsequently serve as additional templates for the same primer sequences, successive rounds of primer annealing, strand elongation, and dissociation may produce rapid and highly-specific amplification of the desired sequence. PCR also may be used to detect the existence of a defined sequence in a DNA sample. In a preferred embodiment of the present invention, the isolate is mixed with primers and suitable PCR reagents. A PCR reaction is then performed, to amplify the reporter nucleic acid.

By way of example, a typical PCR assay (e.g., PCR, reverse transcription PCR, real time PCR, and competitive PCR) might start with two synthetic oligonucleotide primers which are complementary to two regions of the DNA of interest (one for each strand) that is to be amplified. These may be added to the DNA of interest (that need not be pure) in the presence of excess deoxynucleotides (dNTPs) and a thermostable DNA polymerase (e.g., Taq polymerase). In a series of temperature cycles (typically 20-40), the DNA of interest may be repeatedly denatured (at ~90° C.), and annealed to the primers (typically at ~40-65° C.), and a daughter strand may be extended from the primers (typically at ~72° C.). As the daughter strands themselves act as templates for subsequent cycles, DNA fragments matching both primers are amplified exponentially, rather than linearly. The target DNA need be neither pure nor abundant; thus, PCR is widely used not only in research, but in clinical diagnostics.

As discussed above, the reporter nucleic acid(s) may comprise a site of relevance in a biological process, such as amplification, transcription, or translation. For example, the reporter nucleic acid(s) may comprise a primer binding site. The system and method of the present invention are advantageous in that they do not require the design of specific primers; rather, any universal primer may be used to amplify the reporter nucleic acid(s), provided that there is a binding site for that primer on the reporter nucleic acid(s). Primers for use in the method of the present invention may also be species- or taxon-specific;

In one embodiment of the present invention, at least one primer used in the polymerase chain reaction (PCR) or isothermal amplification is labeled with a detectable agent. As used herein, an "agent" shall include a protein, polypeptide, peptide, nucleic acid (including DNA or RNA), antibody, Fab fragment, $F(ab')_2$ fragment, molecule, compound, antibiotic, drug, and any combinations thereof. A Fab fragment is a univalent antigen-binding fragment of an antibody, which is produced by papain digestion. A $F(ab')_2$ fragment is a divalent antigen-binding fragment of an antibody, which is produced by pepsin digestion.

A primer may be labeled with a detectable agent using one of a variety of labeling techniques, including peroxidase, chemiluminescent labels known in the art, and radioactive labels known in the art. The detectable agent of the present invention may be, for example, a nonradioactive or fluorescent marker, such as biotin, fluorescein (FITC), acridine, cholesterol, or carboxy-X-rhodamine, which can be detected using fluorescence and other imaging techniques readily known in the art. Alternatively, the detectable marker may be a radioactive marker, including, for example, a radioisotope. The radioisotope may be any isotope that emits detectable radiation, such as $^{35}S$, $^{32}P$, or $^{3}H$. Radioactivity emitted by the radioisotope can be detected by techniques well known in the art. For example, gamma emission from the radioisotope may be detected using gamma imaging techniques, particularly scintigraphic imaging. Additional detectable agents include, without limitation, tags (e.g., fluorescent tags, IR tags, mass-code tags, MS tags, potentiometric tags, and UV tags), dyes, and antigens.

In accordance with the method of the present invention, detection of target nucleic acid sequences is achieved by hybridization. The capture nucleic acid and the reporter nucleic acid bind to the target sequence, whether the capture nucleic acid is pre-bound to a solid phase, or is bound to the solid phase during the detection process. The capture oligonucleotide detects the reporter nucleic acid that matches the target nucleic acid sequence, and isolates the matching reporter nucleic acid from among the other, non-matching, reporter nucleic acids. In the present method, PCR may be used only to detect the isolated reporter nucleic acid. Two arbitrary primer sequences may be present in the synthetic reporter nucleic acid. Primer sequences may be the same for all reporter nucleic acids; however, the distance between them will be different in different reporter nucleic acids. In this manner, the size/length of the amplified product will code for the target nucleic acid sequence originally present in the sample. Detection may be achieved using any reporter system that can discriminate based on size (e.g., sequencer, mass spectrometry, etc.).

The DNA fragments that are products of the PCR or isothermal amplification reaction may be separated (e.g., according to size) and detected, and the presence or absence of the reporter nucleic acid may be determined, using standard methods known in the art, including, without limitation, gel electrophoresis (such as agarose gel electrophoresis, polyacrylamide gel electrophoresis, and capillary gel electrophoresis), chromatography (such as high-performance liquid chromatography (HPLC) and gas chromatography (GC)), spectrometry (such as mass spectrometry (MS) and GC-MS), infra-red spectrometry, and UV spectrometry), spectrophotometry (such as fluorescence spectrophotometry), atmospheric pressure chemical ionization mass spectroscopy, potentiostatic amperometry, immunoassays (such as ELISA), electrochemical detection, and melting-curve analysis.

In one embodiment of the present invention, the DNA fragments are separated according to size using gel electrophoresis (e.g., polyacrylamide gel electrophoresis or capillary gel electrophoresis) or HPLC, and then the reporter nucleic acid is detected using electrochemical detection or UV detection. In another embodiment, the DNA fragments are separated according to size using capillary gel electrophoresis or MS/GC-MS, and then the reporter nucleic acid is detected using electrochemical detection or MS.

HPLC is a chromatographic separation technique that separates compounds that are dissolved in solution. A number of HPLC techniques, including IP-RO-HPLC on non-porous PS/DVB particles with chemically-bonded alkyl chains, have been shown to be good alternatives to capillary electrophoresis in the analysis of both single- and double-strand nucleic acids, providing similar degrees of resolution. See, e.g., Huber et al., *Anal. Biochem.*, 212:351, 1993; Huber et al., *Nuc. Acids Res.*, 21:1061, 1993; Huber et al., *Biotechniques*, 16:898, 1993). In contrast to ion-exchange chromatography, which does not always retain double-strand DNA as a function of strand length, IP-RP-HPLC enables a strictly size-dependent separation. For example, it is known to separate PCR products differing only 4-8 base pairs in length, within a size range of 50 to 200 nucleotides (Oefner et al., *Anal. Biochem.*, 223:39, 1994).

Capillary electrophoresis (CE) is a method particularly suitable for rapid, high-resolution separation of components of a complex mixture. CE involves separations on a parallel array of capillaries, and may take various forms, including free solution, isotachophoresis, isoelectric focusing, polyacrylamide gel, and micellar electrokinetic chromatography. When combined with MS, CE is a powerful technique for bioanalysis, often offering resolution several orders of magnitude higher than those of traditional techniques (Smith et al., *J. Chromatog.*, 480:211, 1989; Grese et al, *J. Am. Chem. Soc.*, 111:2835, 1989). Capillary electrophoresis may have a number of applications, including high-throughput screening or sequencing.

In one preferred embodiment, detection of amplification products may be achieved through use of the Masscode® (QIAGEN Genomics, Inc., Bothell, Wash.) technology (Kokoris et al., High-throughput SNP genotyping with the Masscode system. *Mol. Diagn.*, 5(4):329-40, 2000). In this embodiment, individual primers may be conjugated with a unique mass-code tag, through a photocleavable linkage. Photocleavage of the mass-code tag from the purified PCR product, along with mass-spectrometric analysis, will permit identification of the amplified reporter nucleic acid target through the two molecular weights assigned to the forward primer and the reverse primer, respectively.

The method of the invention is beneficial for a number of reasons. For example, in the initial step of target-sequence binding, the long oligonucleotides are more flexible with respect to hybrid melting temperatures than are the shorter primers used for consensus PCR. Therefore, broad-based capture is enabled, without sacrificing sensitivity. A correlation between numbers of targets and the templates carried forward into PCR or into isothermal amplification can also facilitate standardization for target quantification.

By way of example, a low-tech detection procedure may be carried out in a reaction tube. To begin, nucleic acid is isolated from a sample. RNA and DNA, for example, may be isolated using silica. Mixtures of capture and reporter nucleic acids may be hybridized to the target nucleic acid sequence(s) potentially present in the isolated nucleic acid. Capture nucleic acids may be bound to the solid phase (e.g., a biotinylated capture nucleic acid is bound to streptavidin-coated magnetic beads), and then washed. Unbound reporter oligonucleotides, for which no matching target sequence is present in the nucleic acid sample, may be removed. The PCR master mix, containing two primers represented in the reporter nucleic acids, may be added, and the mixture may be amplified in the reaction tube. Product size may then be analyzed. By virtue of this step, the identity of any target sequence present in the nucleic acid sample may also be analyzed.

Additionally, and by way of example, a high-tech detection procedure may be carried out in a microfluidics device (e.g., a microfluidics chamber comprising various reporter nucleic acids of differing lengths and specific PCR primers used for amplification). To begin, nucleic acid may be isolated from a sample, as described above. The isolated nucleic acid may be loaded into the microfluidics device, and one or more target nucleic acid sequences potentially present in the isolated nucleic acid may be hybridized to capture nucleic acids that are covalently bound to the chamber surface. Reporter nucleic acids may be loaded into the chamber, and hybridized to target nucleic acid sequences that were bound to matching capture nucleic acids during the initial step. Capture nucleic acids may then be washed to remove unbound reporter nucleic acids for which no matching target sequence was present in the nucleic acid sample. The PCR master mix, containing two primers represented in the reporter nucleic acids, may be added, and the mixture may be amplified in the microfluidics device. Product size may then be analyzed. By virtue of this step, the identity of any target sequence present in the nucleic acid sample is also analyzed.

In the method of the present invention, PCR analysis in the amplification step does not require primers that match the target sequence. Rather, detection by hybridization can accommodate differences (i.e., mutations) in a sequence, even up to a 20% difference. Accordingly, the inventors' system and method are suitable for the detection of new sequences and for the detection of sequences that are related to known sequences (i.e., the sequences that are used to design primers or oligonucleotides). In applications where new targets are queried, reporter nucleic acids may be released from the solid support by washes of increasing stringency. PCR of the different fractions may then be performed in a different compartment, where low stringency may be used for unspecific or distantly-related sequences, medium stringency may be used for closely-related sequences, and high stringency may be used for highly-specific identical sequences. For low-tech detection, then, the solid support may be washed with increasing stringency, after unbound reporter nucleic acids are removed. Each eluate may then be analyzed by PCR in a separate tube. For high-tech detection, the solid support may be washed with increasing stringency, after unbound reporter nucleic acids are removed. Each eluate may then be analyzed in a microfluidics PCR chamber printed on the same chip. By way of example, one eluate after the other may be analyzed; alternatively, eluates may be analyzed in a parallel arrangement using (e.g., using three PCR chambers).

It is also within the confines of the present invention for detection of target sequences to be integrated into a microfluidics device. In addition to sequences of different lengths, sequences having different base compositions may be inserted between the primer binding sites of the reporter nucleic acids. In this manner, the amplified products may be distinguished by sequence. Detection may be achieved by hybridization to complementary nucleic acids, using labeled nucleotides during PCR. For example, a fluorescence or digoxigenin/biotin label would permit detection via enzymatic dye generation. Complementary nucleic acids may be printed in distinct dots or bands in a microfluidics chamber situated near the PCR amplification chamber. The location of hybridization, as indicated through fluorescence or dye development, identifies the sequence of the reporter, thereby identifying the original target sequence present in the nucleic acid sample.

Additionally, a disclosed herein, a detecting system for use in the method of the present invention need not comprise a capture nucleic acid that is already pre-bound to the solid support. Rather, in some embodiments, the capture nucleic acid is not pre-bound to the solid support, but may become bound to the solid support during the detection process. Accordingly, the present invention further provides a method for determining the presence or absence of a target nucleic acid sequence in a sample, comprising the steps of: (a) obtaining a detecting system comprising: (i) a capture nucleic acid that is capable of binding to a first region of the target nucleic acid sequence; (ii) a reporter agent that is capable of binding to a second region of the target nucleic acid sequence, comprising at least one reporter nucleic acid; and (iii) a solid support capable of specifically binding to the capture nucleic acid; (b) contacting the sample with the capture nucleic acid and the reporter agent, under conditions suitable for formation of a complex comprising the target nucleic acid sequence, the capture nucleic acid, and the reporter nucleic acid; (c) isolating, if any, a complex comprising the target nucleic acid sequence, the capture nucleic acid, and the reporter nucleic acid; (d) amplifying the reporter nucleic acid or a portion thereof in the complex; (e) binding the capture nucleic acid to the solid support; and (f) determining the presence or absence of the reporter nucleic acid or portion thereof. In accordance with this method of the present invention, the target nucleic acid sequence is present in the sample if the reporter nucleic acid or portion thereof is present; the target nucleic acid sequence is absent from the sample if the reporter nucleic acid or portion thereof is absent.

The present invention also provides a complex, comprising a target nucleic acid sequence, a capture nucleic acid, and a reporter nucleic acid. In one embodiment, the complex further comprises a solid support.

As discussed above, the detecting system described herein is also sensitive enough and flexible enough to support multiplex detection of multiple target nucleic acid sequences in a sample. Accordingly, the present invention also provides a method for determining the presence or absence of one or more—preferably, multiple—target nucleic acid sequences in a sample, comprising the steps of: (a) obtaining a detecting system comprising a plurality of subsystems, wherein each subsystem comprises: (i) a capture nucleic acid that is pre-bound to a solid support and is capable of binding to a first region of a target nucleic acid sequence in the sample; and (ii) a reporter agent that is capable of binding to a second region of the same target nucleic acid sequence in the sample, comprising at least one reporter nucleic acid; (b) contacting the sample with the detecting system, under conditions suitable for formation of at least one complex comprising a capture nucleic acid, a reporter agent, and a target nucleic acid sequence; (c) isolating, if any, at least one complex comprising a target nucleic acid sequence, a capture nucleic acid, and a reporter nucleic acid; (d) amplifying the reporter nucleic acid or a portion thereof in the at least one complex; and (e) determining the presence or absence of the reporter nucleic acid or portion thereof. The target nucleic acid sequences are present in the sample if the corresponding reporter nucleic acids, or portions thereof, are present; the target nucleic acid sequences are absent from the sample if the corresponding reporter nucleic acids, or portions thereof, are absent.

In one embodiment of the present invention, the capture nucleic acid and the reporter agent in at least one subsystem bind to a target nucleic acid sequence in the sample that is different from the target nucleic acid sequence to which the capture nucleic acid and the reporter agent in at least one other subsystem bind. In another embodiment, at least two subsystems comprise reporter nucleic acids that differ in length. It is conceivable that the various subsystems for use in the present invention may comprise identical reporter nucleic acids. However, in such a case, different primers may be used in the amplification step to assist in the detection of target nucleic acid sequences in the sample. This application may be an economical option where super-sensitivity of the method is not required (e.g., in methods of detecting potentially-harmful contamination in food).

In the contacting step of the above-described method, the sample may be brought into contact with the various components of the various subsystems in different stages. For example, within each subsystem, the sample may be contacted with the capture nucleic acid of the detecting system prior to, at the same time as, or following the contacting of the reporter nucleic acid with the sample. Furthermore, the sample may be brought into contact with each subsystem in a sequential manner or in a concurrent manner. It is even within the confines of the present invention for the sample to be brought into contact with all capture nucleic acids of the subsystems prior to contact with all reporter nucleic acids of the subsystems, or vice versa.

The above-described method for detecting multiple target nucleic acid sequences in a sample may also utilize a detecting system in which the capture nucleic acid is not already bound to the solid support. Accordingly, the present invention further provides a method for determining the presence or absence of one or more—preferably, multiple—target nucleic acid sequences in a sample, comprising the steps of: (a) obtaining a detecting system comprising a plurality of subsystems, wherein each subsystem comprises: (i) a capture nucleic acid that is capable of binding to a first region of a target nucleic acid sequence in the sample; (ii) a reporter agent that is capable of binding to a second region of the same target nucleic acid sequence in the sample, comprising at least one reporter nucleic acid; and (iii) a solid support capable of specifically binding to the capture nucleic acid; (b) contacting the sample with the detecting system, under conditions suitable for formation of at least one complex comprising a capture nucleic acid, a reporter agent, and a target nucleic acid sequence; (c) isolating, if any, at least one complex comprising a target nucleic acid sequence, a capture nucleic acid, and a reporter nucleic acid; (d) amplifying the reporter nucleic acid or a portion thereof in the at least one complex; (e) binding the capture nucleic acid in each subsystem to the solid support in each subsystem; and (f) determining the presence or absence of the reporter nucleic acid or portion thereof. The target nucleic acid sequences are present in the sample if the corresponding reporter nucleic acids, or portions thereof, are present; the target nucleic acid sequences are absent from the sample if the corresponding reporter nucleic acids, or portions thereof, are absent.

The present invention is described in the following Examples, which are set forth to aid in the understanding of the invention, and should not be construed to limit in any way the scope of the invention as defined in the claims which follow thereafter.

EXAMPLES

Example 1

FLAReS Protocol

Figure 2:
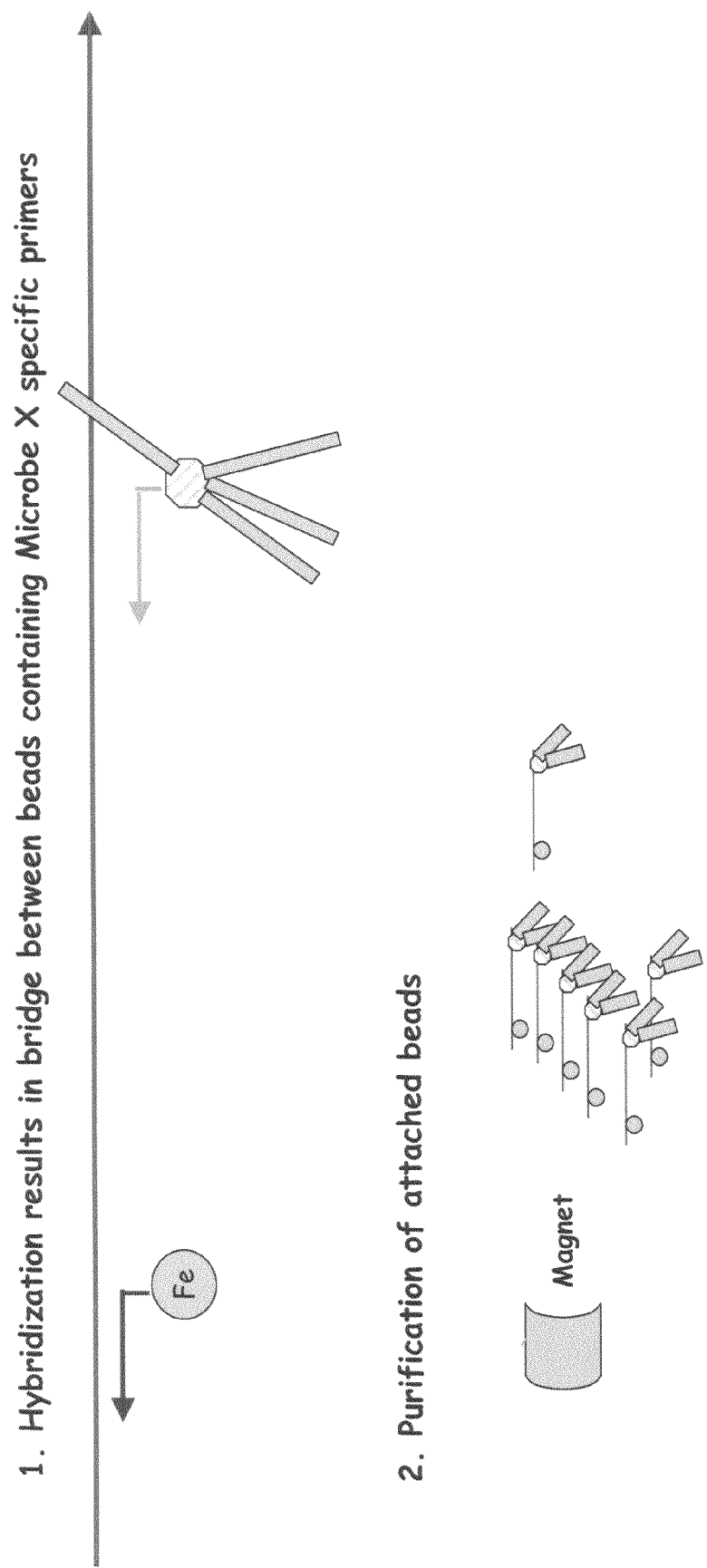
FIG. 2 sets forth a magnetic purification strategy for use in FLAReS.
Figure 2:
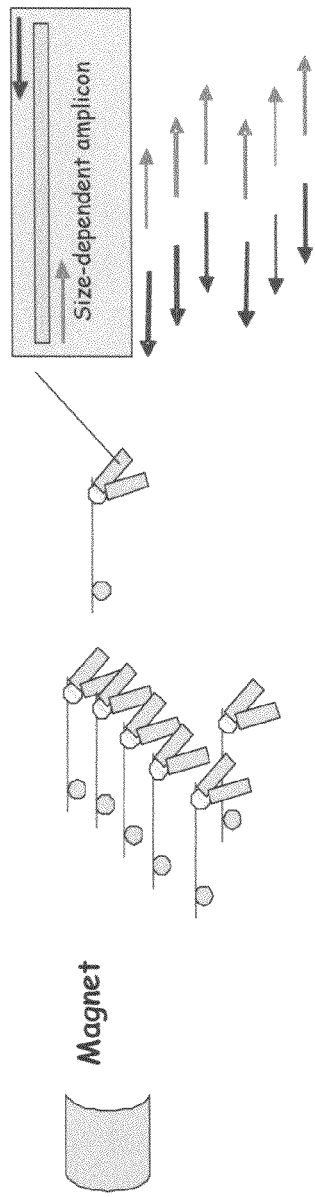

As demonstrated in FIGS. 1-3, the fragment-length amplification reporting system (FLAReS) is based on a strategy for enrichment of a reporter template for use in PCR and other gene-amplification methods (e.g., isothermal amplification). This is achieved by hybridization, in solution, of two different populations of variably-degenerate polynucleotides complementary to two different regions on the same nucleic acid strand of a target sequence (e.g., a microbial genome or mRNA). One polynucleotide population (the capture polynucleotide) is immobilized on a solid support or substrate (e.g., a magnetic bead, a chromatographic substrate, or a microfluidic substrate). The other population (the reporter polynucleotide) contains both a sequence complementary to a region of the target different from that of the capture polynucleotide, and a sequence that includes polymerase binding sites for initiating PCR (forward and reverse primer binding sites) or isothermal (a 5' T7 binding site and a 3' transcription termination site) amplification. Binding of both types of polynucleotides (capture and reporter) to the target sequence results in a bridge that facilitates separation of specific reporter polynucleotides from all other non-reactive reporter polynucleotides.

Each reporter polynucleotide consists of a single molecule, wherein the portion hybridizing to the target is linked (e.g., via a bead, a chemical linker, or a stretch of inert nucleotides) to a construct containing sequences that bind primers (e.g., for polymerase chain reaction) or polymerases (e.g., for isothermal amplification). The sequences for polymerase chain reaction or isothermal amplification do not vary with the target. However, the template size is distinctive for each potential target (e.g., microbe or host transcript). Therefore, the assay's specificity depends upon discrete changes in the length of an amplification product. This allows for size-coded identification of nucleic acid targets.

Modifications are introduced into the assay, as desired. For example, the FLAReS system may be modified to alter specificity of the method, using related, but not identical, capture polynucleotides to allow detection of sequences that differ from the ideal target. This modification is useful for the identification of novel genes or microbes. Additionally, the FLAReS system may be modified to enhance the signal, using the same reporter polynucleotide in conjunction with capture oligonucleotides that hybridize to different regions on the same nucleic acid target. This modification is useful where targets are present in low copy number. Furthermore, the FLAReS system may be modified to confirm detection of a microbe or host transcript, using two independent capture polynucleotide sets that bind different regions of the same target and yield different amplification products.

Example 2

FLAReS Detection Process: General Methodology

Detection of target sequences is achieved by hybridization. A "capture oligonucleotide" and a "reporter oligonucleotide" bind to the target sequence. Capture oligonucleotides are either pre-bound to a solid phase, or are bound to the solid phase during the detection process. In either case, the capture oligonucleotide detects the reporter oligonucleotide that matches the target sequence, and isolates the matching reporter from among the other, non-matching, reporter oligonucleotides.

In the FLAReS system, PCR is used only to detect the isolated reporter oligonucleotide. Two arbitrary primer sequences are present in the synthetic reporter oligonucleotide. Primer sequences are the same for all reporter oligonucleotides; however, the distance between them is different in different reporter oligonucleotides. In this manner, length of the amplified product codes for the target sequence originally present in the sample.

Example 3

FLAReS Detection Process: Low-Tech Methodology

A low-tech detection procedure is carried out in a reaction tube. To begin, nucleic acid (na) is isolated from a sample. For example, RNA and DNA may be isolated using silica. Mixtures of capture and reporter oligonucleotides are hybridized to the target sequence(s) potentially present in the isolated na. Capture oligonucleotides are bound to the solid phase (e.g., a biotinylated capture oligonucleotide is bound to streptavidin-coated magnetic beads), and then washed. Unbound reporter oligonucleotides, for which no matching target sequence was present in the na sample, are removed. The PCR master mix, containing the two primers represented in the reporter oligonucleotides, is added, and the mixture is amplified in the reaction tube. Product size is then analyzed. By virtue of this step, the identity of any target sequence present in the na sample is also analyzed. When product size is analyzed by gel electrophoresis, amplification is most efficient for products of 50-350 bp; with increasing size, the efficiency (sensitivity) decreases. Assuming resolution in 50-bp steps, 7-plex detection is conceivable.

Example 4

FLAReS Detection Process: High-Tech Methodology

A high-tech detection procedure is carried out in a microfluidics device. To begin, nucleic acid (na) is isolated from a sample. For example, RNA and DNA may be isolated using silica. Isolated na is loaded into the microfluidics device, and one or more target sequences potentially present in the isolated na are hybridized to capture oligonucleotides that are covalently bound to the chamber surface. Reporter oligonucleotides are loaded into the chamber, and hybridized to target sequences that were bound to matching capture oligonucleotides during the initial step. Capture oligonucleotides are then washed to remove unbound reporter oligonucleotides for which no matching target sequence was present in the na sample. The PCR master mix, containing the two primers represented in the reporter oligonucleotides, is added, and the mixture is amplified in the microfluidics device. Product size is then analyzed. By virtue of this step, the identity of any target sequence present in the na sample is also analyzed. When product size is analyzed by capillary electrophoresis, detection of 1-2 bp differences allows 150-plex or higher detection.

Example 5

Detection of New and Related Sequences

In other systems (e.g., mass-tag), PCR analysis requires primers that match the target sequence. Detection by hybridization can accommodate differences in a sequence (i.e., mutations); indeed, hybridization is still efficient for sequences that are only 80-90% identical. FLAReS is suitable for the detection of new sequences and sequences that are related to known sequences (i.e., the sequences that are used to design primers or oligonucleotides). Detection of related sequences bears the risk of unspecific detection. Therefore, in applications where new targets are queried, reporter oligonucleotides are released from the solid phase by washes of increasing stringency. PCR of the different fractions is then performed in a different compartment, where low stringency=unspecific/distantly-related sequences, medium stringency=closely-related sequences, and high stringency=highly-specific identical sequences.

For low-tech detection, the solid phase (beads) is washed with increasing stringency, after unbound reporter oligonucleotides are removed. Each eluate is then analyzed by PCR in a separate tube. For high-tech detection, the solid phase (beads) is washed with increasing stringency, after unbound reporter oligonucleotides are removed. Each eluate is then analyzed in a microfluidics PCR chamber printed on the same chip (e.g., one eluate after the other; in a parallel arrangement using, e.g., three PCR chambers; etc.).

Example 6

Integrated Detection in Microfluidics Device

Detection of target sequences may be integrated into a microfluidics device. In addition to sequences of different lengths, sequences having different base compositions can be inserted between the primer binding sites of the reporter oligonucleotides. In this manner, the amplified products may be distinguished by sequence. Detection is achieved by hybridization to complementary oligonucleotides, using labeled nucleotides during PCR. For example, a fluorescence or digoxigenin/biotin label allows for detection via enzymatic dye generation. Complementary oligonucleotides are then printed in distinct dots or bands in a microfluidics chamber neighboring the PCR amplification chamber. The location of hybridization, as indicated through fluorescence or dye development, identifies the sequence of the reporter, thereby identifying the original target sequence present in the na sample.

Example 7

Use of FLAReS to Detect SARS CoV

The inventors used a 4-plex system (the 3 human coronaviruses and a control), with biotin/magnetic streptavidin beads in the solid phase, to detect SARS CoV with FLAReS.

```
Primer Sequences Included
in Reporter Nucleic Acids:
UniPriL1     CACTCATCCTGGTGCTTCTG    (SEQ ID NO:
                                      1)

UniPriR84    TAAACTTTGTTGGCGGAGGA    (SEQ ID NO:
                                      2)

Capture Nucleic Acids
SARS-N2
                                     (SEQ ID NO: 3)
5'-biotin-GCGCGAGGGCAGTTTCACCACCTCCGCTAGCCATTCGAGC
AGGAGAATTTCCCCTACTGC OC43-N2
                                     (SEQ ID NO: 4)
5'-biotin-TCCCTCCTGATGGTTGCTGAGAGGTAGCAGTTTGCTTGGG
TTGAGCTCTTCTACCCCTGG 229E-N2
                                     (SEQ ID NO: 5)
5'-biotin-AACCTGTAGGTTCAGTTTTAGCACCATCAACAGCAACCCA
GACGACACCTTCAACACGCT Control pGEM-N2
                                     (SEQ ID NO: 6)
5'-biotin-CGCTTCCTCGCTCACTGACTCGCTGCGCTCGGTCGTTCGG
CTGCGGCGAGCGGTATCAGC Detector Nucleic Acids
Atemp61-SARSN1
           (SEQ ID NOs:7 and 8, respectively)
5'-CACTCATCCTGGTGCTTCTGAGGTCCTTGTAGTCATTTATCTCCTCC
GCCAACAAAGTTTA-3'-c9-5'-CCGCGACTACGTGATGAGGAGCGAGA
AGAGGCTTGACTGCCGCCTCTGCTTCCCTCTGC-3'

Atemp77-OC43N1
           (SEQ ID NOs:9 and 10, respectively)
5'-CACTCATCCTGGTGCTTCTGAGGTCCTTGTAGTCATTCAAGGCACCA
TTTATTTATCTCCTCCGCCAACAAAGTTTA-'3-c9-5'-TGGTCGGACT
GATCGGCCCACTTGAGGATGCCATTACCAGAACGATTTCCAGAGGACGCT
-3'

Atemp69-229EN1
           (SEQ ID NOs:11 and 12, respectively)
5'-CACTCATCCTGGTGCTTCTGAGGTCCTTGTAGTCATTCAAGGATTTA
TCTCCTCCGCCAACAAAGTTTA-3'-c9-5'-GGGGTCCTGTGCCAAGAT
AATAAAAATGCAGCTTGGGTGACAAATCCACCCGTTTGCCCT-3'

Atemp84-pGEMN1
           (SEQ ID NOs:13 and 14, respectively)
5'-CACTCATCCTGGTGCTTCTGAGGTCCTTGTAGTCATTCAAGGCACCA
TTTGCGCCGGATTTATCTCCTCCGCCAACAAAGTTTA-3'-c9-5'-TCG
GGAAACCTGTCGTGCCAGCTGCATTAATGAATCGGCCAACGCGCGGGGAG
AGGCGGT-3'
```

While the foregoing invention has been described in some detail for purposes of clarity and understanding, it will be appreciated by one skilled in the art, from a reading of the disclosure, that various changes in form and detail can be made without departing from the true scope of the invention in the appended claims.

What is claimed is:

1. A method for determining the presence or absence of at least one target nucleic acid sequence in a test sample, the method comprising:
   (a) contacting a detecting system, which comprises at least one detecting subsystem, wherein the at least one detecting subsystem comprises:
      at least one capture nucleic acid comprising 40 to 70 consecutive variably degenerate nucleotides complementary to the target nucleic acid sequence or at least one capture nucleic acid comprising consecutive nucleotides complementary to the target nucleic acid sequence, wherein the capture nucleic acid binds to a first region in the target nucleic acid sequence, and
      at least one detector agent which comprises: (i) a binder nucleic acid comprising 40 to 70 consecutive variably degenerate nucleotides complementary to the target nucleic acid sequence, wherein the binder nucleic acid binds to a second region in the target nucleic acid sequence, and (ii) a reporter nucleic acid comprising 50 to 350 nucleotides which is linked to the binder nucleic acid, wherein the reporter nucleic acid further comprises a first primer binding sequence and a second primer binding sequence, wherein the first and the second primer binding sequences are different;
      with the test sample, under conditions suitable for formation of a complex comprising the target nucleic acid sequence, the capture nucleic acid, and the detector agent and forming a mixture;
   (b) immobilizing the capture nucleic acid in the mixture on a solid support;
   (c) washing the solid support to remove unbound detector agent and unbound target nucleic acid and isolate the complex comprising the target nucleic acid sequence, the capture nucleic acid, and the detector agent if the target nucleic acid is present in the test sample;
   (d) adding a first primer which binds to the first primer binding sequence of the reporter nucleic acid and a second primer which binds to a sequence complementary to the second primer binding sequence of the reporter nucleic acid onto the solid support in step (c) and amplifying the reporter nucleic acid or a portion thereof, using the first primer and the second primer to produce an amplified product, wherein detecting the amplified product indicates the presence of the target nucleic acid sequence in the test sample.

2. The method of claim 1, further comprising isolating the complex comprising the target nucleic acid sequence, the capture nucleic acid, and the detector agent, if the target nucleic acid is present in the test sample and said complex is present.

3. The method of claim 1, wherein the solid support is a bead, a chromatographic substrate, or a microfluidics substrate.

4. The method of claim 3, wherein the bead is magnetic.

5. The method of claim 1, wherein the capture nucleic acid is covalently or non-covalently bound to the solid support.

6. The method of claim 1, wherein the capture nucleic acid is directly or indirectly bound to the solid support.

7. The method of claim 1, wherein the 40 to 70 consecutive variably degenerate nucleotides complementary to the target nucleic acid sequence have at least 80% complementarity to the target nucleic acid sequence.

8. The method of claim 1, wherein the capture nucleic acid comprises about 32 to about 41 consecutive variably degenerate nucleotides complementary to the target nucleic acid sequence.

9. The method of claim 1, wherein the at least one detecting subsystem comprises at least two capture nucleic acids, from the at least one capture nucleic acid, and each of the at least two capture nucleic acids binds to a different region of the target nucleic acid sequence.

10. The method of claim 1, wherein the detecting system comprises at least two detecting subsystems, from the at least one detecting subsystem, which have different capture nucleic acids that bind different regions of the target nucleic acid sequence and different reporter nucleic acids which yield different amplified products.

11. The method of claim 1, wherein the first primer binding sequence comprises 15 to about 20 nucleotides and the second primer binding sequence comprises 15 to about 20 nucleotides.

12. The method of claim 1, wherein the at least one detecting subsystem comprises at least two detecting subsystems comprising different reporter nucleic acids, and the first primer binding sequence of each of the different reporter nucleic acids is identical.

13. The method of claim 1, wherein the at least one detecting subsystem comprises at least two detecting subsystems comprising different reporter nucleic acids, and the second primer binding sequence of each of the different reporter nucleic acids is identical.

14. The method of claim 1, wherein the target nucleic acid sequence comprises DNA or RNA.

15. The method of claim 1, wherein the detecting step further comprises analyzing the size of the amplified product.

16. The method of claim 15, wherein the size of the amplified product is resolved by capillary electrophoresis.

17. The method of claim 1, further comprising analyzing the sequence of the amplified product.

18. The method of claim 1, wherein the at least one detecting subsystem comprises at least two detecting subsystems comprising different reporter nucleic acids, and wherein the different reporter nucleic acids of the at least two detecting subsystems are capable of producing amplified products with different lengths.

19. The method of claim 1, wherein the at least one detecting system comprises at least two detecting subsystems comprising different reporter nucleic acids, wherein the different reporter nucleic acids in the at least two detecting subsystems comprise first and second primer binding sequences, and wherein the distance between the first and second primer binding sequences is different in each of the different reporter nucleic acids.

20. The method of claim 1, wherein the detecting system consists of one detecting subsystem.

21. The method of claim 1, wherein the binder nucleic acid comprises 40 consecutive variably degenerate nucleotides complementary to the target nucleic acid sequence.

22. The method of claim 1, wherein the at least one detecting subsystem comprises at least two detecting subsystems comprising different reporter nucleic acids, and wherein the different reporter nucleic acids of the at least two detecting subsystems have nucleotide sequences with different base composition.

23. The method of claim 1, wherein the amplifying step is performed in a microfluidic device.

24. The method of claim 1, wherein the at least one detecting subsystem comprises at least two detecting subsystems comprising different capture nucleic acids, and wherein the different capture nucleic acids in the at least two detecting subsystems are capable of binding to different target nucleic acid sequences when the different target nucleic acid sequences are present in the test sample.

25. The method of claim 1, wherein the at least one detecting system comprises at least two detecting subsystems comprising different reporter nucleic acids, and wherein the different reporter nucleic acids of the at least two detecting subsystems are different in length.

26. The method of claim 1, wherein said amplifying the reporter nucleic acid or portion thereof is amplified using polymerase chain reaction or isothermal amplification.

27. The method of claim 26, wherein the first primer or the second primer is labeled with an agent selected from the group consisting of a fluorescein, a mass-code tag, a radioactive isotope, a dye, and an antigen.

28. The method of claim 1, wherein the amplified product is detected using a technique selected from the group consisting of chromatography, gel electrophoresis, mass spectroscopy, and spectrophotometry.

29. The method of claim 28, wherein the gel electrophoresis is capillary gel electrophoresis.

30. The method of claim 1, wherein the at least one target nucleic acid sequence in the sample is related to a pathological condition in a subject or is derived from a pathogen.

31. The method of claim 1, wherein the test sample is a biological sample, or an environmental sample, or a food sample.

32. The method of claim 1, wherein the reporter nucleic acid further comprises at least one site selected from the group consisting of a polymerase binding site, a transcription termination site, and a restriction enzyme site.

33. The method of claim 1, wherein the reporter nucleic acid is linked to the binder nucleic acid by a solid substance, a bead, a fiber, a chemical linker, at least one amino acid, or at least one nucleotide.

34. The method of claim 1, wherein the binder nucleic acid comprises a sequence that is completely complementary to a sequence of the second region of the target nucleic acid sequence.

35. The method of claim 1, wherein the binder nucleic acid is capable of hybridizing under high-stringency conditions to the second region of the target nucleic acid sequence.

36. The method of claim 1, wherein the target nucleic acid sequence comprises a nucleic acid sequence from a SARS CoV, an influenza virus, a *M. pneumoniae*; a West Nile virus, a St. Louis encephalitis virus (SLEV), a Dengue type 1 virus, a Dengue type 2 virus, a Dengue type 3 virus, a Dengue type 4 virus, a bunyamwera virus, a California encephalitis serogroup of the bunyaviruses, a Venezuelan equine encephalitis virus serotype, a respiratory syncytial virus group A, and a respiratory syncytial virus group B.

37. The method of claim 1, wherein the at least one detector agent consists of one detector agent.

38. The method of claim 1, wherein the first primer or the second primer is a synthetic primer.

39. The method of claim 1, wherein the immobilizing of the capture nucleic acid in step (b) is performed before step (a).

* * * * *

SEQUENCE LISTING

<160> NUMBER OF SEQ ID NOS: 14

<210> SEQ ID NO 1
<211> LENGTH: 20
<212> TYPE: DNA
<213> ORGANISM: artificial sequence
<220> FEATURE:
<223> OTHER INFORMATION: primer included in reporter nucleic acid

<400> SEQUENCE: 1
cactcatcct ggtgcttctg             20

<210> SEQ ID NO 2
<211> LENGTH: 20
<212> TYPE: DNA
<213> ORGANISM: artificial sequence
<220> FEATURE:
<223> OTHER INFORMATION: primer included in reporter nucleic acid

<400> SEQUENCE: 2
taaactttgt tggcggagga             20

<210> SEQ ID NO 3
<211> LENGTH: 60
<212> TYPE: DNA
<213> ORGANISM: artificial sequence
<220> FEATURE:
<223> OTHER INFORMATION: capture nucleic acid

<400> SEQUENCE: 3
gcgcgagggc agtttcacca cctccgctag ccattcgagc aggagaattt cccctactgc             60

<210> SEQ ID NO 4
<211> LENGTH: 60
<212> TYPE: DNA
<213> ORGANISM: artificial sequence
<220> FEATURE:
<223> OTHER INFORMATION: capture nucleic acid

<400> SEQUENCE: 4
tccctcctga tggttgctga gaggtagcag tttgcttggg ttgagctctt ctacccctgg             60

<210> SEQ ID NO 5
<211> LENGTH: 60
<212> TYPE: DNA
<213> ORGANISM: artificial sequence
<220> FEATURE:
<223> OTHER INFORMATION: capture nucleic acid

<400> SEQUENCE: 5
aacctgtagg ttcagtttta gcaccatcaa cagcaaccca gacgacacct tcaacacgct             60

<210> SEQ ID NO 6
<211> LENGTH: 60
<212> TYPE: DNA
<213> ORGANISM: artificial sequence
<220> FEATURE:
<223> OTHER INFORMATION: capture nucleic acid - control

<400> SEQUENCE: 6
cgcttcctcg ctcactgact cgctgcgctc ggtcgttcgg ctgcggcgag cggtatcagc             60

<210> SEQ ID NO 7
<211> LENGTH: 61
<212> TYPE: DNA

```
<213> ORGANISM: artificial sequence
<220> FEATURE:
<223> OTHER INFORMATION: first nucleic acid sequence of detector

<400> SEQUENCE: 7
cactcatcct ggtgcttctg aggtccttgt agtcatttat ctcctccgcc aacaaagttt     60
a                                                                     61

<210> SEQ ID NO 8
<211> LENGTH: 59
<212> TYPE: DNA
<213> ORGANISM: artificial sequence
<220> FEATURE:
<223> OTHER INFORMATION: second nucleic acid sequence of detector

<400> SEQUENCE: 8
ccgcgactac gtgatgagga gcgagaagag gcttgactgc cgcctctgct tccctctgc      59

<210> SEQ ID NO 9
<211> LENGTH: 75
<212> TYPE: DNA
<213> ORGANISM: artificial sequence
<220> FEATURE:
<223> OTHER INFORMATION: first nucleic acid sequence of detector

<400> SEQUENCE: 9
cactcatcct ggtgcttctg aggtccttgt agtcattcaa ggcaccattt atttatctcc     60
tccgccaaca aagtt                                                      75

<210> SEQ ID NO 10
<211> LENGTH: 60
<212> TYPE: DNA
<213> ORGANISM: artificial sequence
<220> FEATURE:
<223> OTHER INFORMATION: second nucleic acid sequence of detector

<400> SEQUENCE: 10
tggtcggact gatcggccca cttgaggatg ccattaccag aacgatttcc agaggacgct     60

<210> SEQ ID NO 11
<211> LENGTH: 69
<212> TYPE: DNA
<213> ORGANISM: artificial sequence
<220> FEATURE:
<223> OTHER INFORMATION: first nucleic acid sequence of detector

<400> SEQUENCE: 11
cactcatcct ggtgcttctg aggtccttgt agtcattcaa ggatttatct cctccgccaa     60
caaagttta                                                             69

<210> SEQ ID NO 12
<211> LENGTH: 60
<212> TYPE: DNA
<213> ORGANISM: artificial sequence
<220> FEATURE:
<223> OTHER INFORMATION: second nucleic acid sequence of detector

<400> SEQUENCE: 12
ggggtcctgt gccaagataa taaaaatgca gcttgggtga caaatccacc cgtttgccct     60

<210> SEQ ID NO 13
<211> LENGTH: 84
<212> TYPE: DNA
<213> ORGANISM: artificial sequence
<220> FEATURE:
```

-continued

```
<223> OTHER INFORMATION: first nucleic acid sequence of detector

<400> SEQUENCE: 13
cactcatcct ggtgcttctg aggtccttgt agtcattcaa ggcaccattt gcgccggatt    60
tatctcctcc gccaacaaag ttta                                           84

<210> SEQ ID NO 14
<211> LENGTH: 60
<212> TYPE: DNA
<213> ORGANISM: artificial sequence
<220> FEATURE:
<223> OTHER INFORMATION: second nucleic acid sequence of detector

<400> SEQUENCE: 14
tcgggaaacc tgtcgtgcca gctgcattaa tgaatcggcc aacgcgcggg gagaggcggt    60
```